United States Patent [19]

Hvid

[11] Patent Number: Plant 6,186

[45] Date of Patent: May 24, 1988

[54] BEGONIA PLANT NAMED 'LISA'

[75] Inventor: Soeren Hvid, Aarup, Denmark

[73] Assignee: L. Daehnfeldt A/S, Odense, Denmark

[21] Appl. No.: 871,218

[22] Filed: Jun. 5, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Olson and Olson

[57] ABSTRACT

A new and distinctive cultivar of begonia plant named Lisa characterized in that it is a rather high, medium broad and medium branching mutation of the cultivar Pia Elise with large double light red flowers which do not significantly fade under abnormal conditions, the flower color pleasantly contrasting with dark green foliage, a vigorous growth habit, and by its ease of manipulation for year around flower production especially well suited for larger containers and hanging baskets for interior decoration.

1 Drawing Sheet

BACKGROUND OF THE INVENTION

This invention relates to a new and distinctive cultivar of begonia plant known botanically as begonia hiemalis Begonia (Fotsch) and known by the cultivar name Lisa.

This new cultivar was discovered by me as a mutation of Pia Elise observed in a group of plants.

Asexual reproduction by stem and/or leaf cuttings has reproduced the unique features of the new cultivar through successive propagations.

The following characteristics distinguish the new begonia from both its parents and other begonias commercially known and used in the floriculture industry:

(1) Compared to Pia Elise, of which the color of the flowers is HCC 19/1–19/2, Lisa has color HCC 19 on the top side of the flower leaf and HCC 620–620/1 on the underside of the leaf.

(2) The flowers are double and have the same size as Pia Elise.

(3) In all other ways the mutation has almost the same "orphological appearance" as Pia Elise, with the exception of the leaves, which are a little smaller.

(4) The new cultivar is considered to be highly floriferous. The stems on which flowering occurs tend to have initiation and development at several nodes at one time.

(5) The keeping qualities of the flowers and the foliage in all seasons allows production and sales efficiencies to be maximized.

(6) The new cultivar tends to be very vigorous so that 10 cm. pot production is best done with shoot cuttings and tip pinching.

(7) Propagation by leaf cuttings is difficult under light and high temperatures in summer months. Stem cuttings can readily be produced in this season.

(8) The flowers of Lisa undergo little or no fading under abnormal conditions. Lisa is also very superior with respect to keeping qualities of winter crops of hiemalis begonias.

THE DRAWING

The accompanying color photograph illustrates the overall appearance of this cultivar taken as a face view of the plant and showing the colors as true as it is reasonably possible to obtain in a colored reproduction of this type.

DESCRIPTION OF THE NEW VARIETY

The following is a detailed description of my new begonia cultivar based on plants produced under commercial practices in glasshouses in various places in Denmark. Color references are made to The Royal Horticultural Society Colour Chart, except where general color terms of ordinary dictionary significance are used.

Parentage: A mutation of the cultivar Pia Elise.

Propagation:

*Type cutting.*—Stem cutting.

*Time to root.*—27–30 days at 21° C. in summer; 25–28 days at 21° C. in winter.

*Rooting habit.*—Uniform, dentritic, fibrous.

*Time for shoot development of leaf cuttings.*—70–85 days to develop adventitious shoots 5–6 cm. (1.96–2.37 inches) long from stick date.

THE PLANT

Form: Low bush type, self-branching, herbaceous.

Habit of growth: Generally rapid, vigorous with strong stems, strong peduncles and strong pedicels.

Foliage: Leaves simple, alternate, borne on vigorous petioles, firm.

(1) *Size.*—Average leaf at maturity from 9–11 cm. (3.54–4.3 inches) long. Leaves may be larger or smaller depending on density of leaf canopy.

(2) *Shape.*—Ovate, slightly concave.

(3) *Texture.*—Leaf is firm, top glabrous, underside rugose.

(4) *Margin.*—Crenate.

(5) *Color.*—Young foliage top side; green 137 D under side; yellow-green 146 D. Mature foliage top side; darker than yellow-green 147 A. under side; yellow-green 147 B to 148 A.

(6) *Veination.*—Palmate.

THE FLOWER

Flowering habits: Flowering in racemes, with several clusters arising from the stem nodes at the same time giving a highly floriferous appearance. Flowering is continuous for a long period of time.

Natural flowering season: Flowering occurs naturally with shortened days lengths beginning mid-September and continuing through May. Reducing day length in summer speeds up flower initiation.

Flower bud: Flat round, progressively deepening in color until tepals begin to open.

Flowers borne: On vigorous peduncles and pedicles in a raceme. The extra doubleness of the flowers causes a pendulous appearance because of the weight of the flowers.

Quantity: Very floriferous, often having 18–20 flowers per main stem in flowering stage at one time.

Tepals:

(1) *Shape.*—Nearly circular.

(2) *Color.*—Top side in winter when opening: HCC 19/1–HCC 622/1. fading to: HCC 19/1–19/2 to HCC 622/1. under side: HCC 622/1.

(3) *Number.*—14–26.

(4) *Size.*—4 Basal tepals 25–30 mm (1.0–1.2 inch), interior tepals 10–20 mm ( 0.4–0.75 inch).

(5) *Flower size.*—5–7 cm (2–2.75 inches).

Reproductive organs:

*Stamens.*—None; cultivar is sterile.

Disease resistance: No particular increase in resistance to disease observed to date.

Additional characteristics: Lisa is a rather high plant, medium broad and medium branching.

I claim:

1. A new and distinct cultivar of Begonia plant named Lisa, as shown and described, comprising a flower color mutation of the cultivar Pia Elise, and particularly characterized by its large double light red flowers, which do not significantly fade under abnormal conditions, with the flower color pleasantly contgrasting with the dark green foliage, vigorous growth habit and by its ease of manipulation for year around flower production, especially for larger containers and hanging baskets for interior decorating.

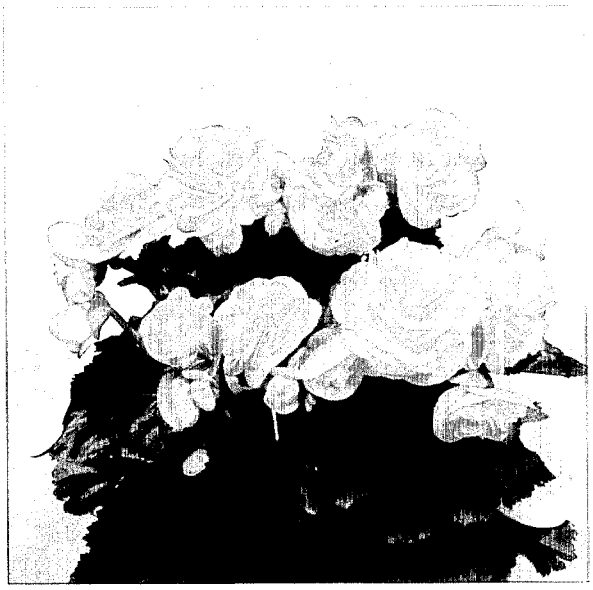

* * * * *